United States Patent [19]

Gindler et al.

[11] 4,239,649

[45] Dec. 16, 1980

[54] CHOLESTEROL STANDARD

[75] Inventors: E. Melvin Gindler; Louis M. Mezei, both of Rockford, Ill.

[73] Assignee: Sherwood Medical Industries Inc., St. Louis, Mo.

[21] Appl. No.: 6,377

[22] Filed: Jan. 25, 1979

[51] Int. Cl.$^3$ .................. G01N 33/16; C09K 3/00
[52] U.S. Cl. .................. 252/408; 23/230 B; 424/3; 435/11; 435/28
[58] Field of Search .................. 252/408; 23/230 B; 424/3; 435/11, 28

[56] References Cited

U.S. PATENT DOCUMENTS

| | | |
|---|---|---|
| 3,260,648 | 7/1966 | Fox .................. 252/408 |
| 3,754,865 | 8/1973 | Gindler .................. 252/408 |
| 3,891,573 | 6/1975 | Stary et al. .................. 252/408 |
| 3,894,844 | 7/1975 | Pinto et al. .................. 252/408 |
| 4,011,045 | 3/1977 | Bonderman .................. 252/408 |

OTHER PUBLICATIONS

Moilliet, J. L. et al., *Surface Activity*, E & F. N. Spon, Ltd., London, p. 357, (1951).

*Primary Examiner*—Teddy S. Gron
*Attorney, Agent, or Firm*—Wegner, Stellman, McCord, Wiles & Wood

[57] ABSTRACT

A cholesterol standard solution containing a predetermined amount of cholesterol, alcohol, and a long chain alkyl substituted betaine.

9 Claims, No Drawings

CHOLESTEROL STANDARD

The present invention relates to a cholesterol standard solution and, more particularly, to a standard solution which has extended mechanical stability and can be fashioned into an aqueous calibrator solution without cholesterol precipitation.

Most cholesterol analyses today are done by mixing a chromogenic working reagent with the sample to be analyzed and, after color development, observing color intensity on a spectrophotometer. The working reagent generally contains cholesterol esterase in order to convert cholesterol esters to free cholesterol and cholesterol oxidase to oxidise free cholesterol yielding cholestenone and simultaneously liberating hydrogen peroxide. Most commonly, the amount of cholesterol present is determined by measuring the amount of hydrogen peroxide liberated using the peroxidase/phenol/4-aminoantipyrine system, which is also present in the working reagent. So that meaningful quantitative information can be obtained, the analysis is also run on calibrator solutions which are prepared by adding the working reagent to standard solutions containing known concentrations of cholesterol.

The procedure, being enzymatic, requires that the working reagent be aqueous. this presents a problem with respect to the preparation of calibrator solutions since cholesterol is substantially insoluble in water. A cholesterol standard solution made up, for example, in alcohol when combined with the aqueous working reagent can form an unacceptable calibrator solution due to precipitation of cholesterol. Such precipitation leads to uncertain color development in the calibrator and generally makes the calibrator solution useless for its intended purpose of reliably correlating color intensity with cholesterol concentration.

Accordingly, a principal object of the present invention is to provide a cholesterol standard solution which, when used to form an aqueous calibrator solution, does not exhibit cholesterol precipitation. A further object resides in providing a cholesterol standard which itself has extended mechanical stability, particularly when subjected to wide fluctuations in temperature.

In accordance with the present invention there is provided a standard solution useful in the quantitative determination of cholesterol consisting essentially of a predetermined amount of cholesterol, a water miscible alcohol, and a long chain alkyl substituted betaine soluble in both alcohol and water. The alcohol is present in an amount sufficient to dissolve the cholesterol to thereby form a solution. The betaine is of a type and present in an amount such that the solution can be fashioned into an aqueous calibrator without cholesterol precipitation.

As used for purposes of the present invention, the term "consisting essentially of" means that the enumerated ingredients must be present, but that other ingredients which do not detract from the desirable attributes of the claimed solution can also be present. For example, water will typically be present in standard solutions formulated in accordance with the present invention. As commercially available, the betaines useful herein are ordinarily supplied as aqueous solutions. Moreover, so long as sufficient alcohol is present to achieve and maintain cholesterol solubility, it is economically more attractive to use water as a diluent rather than excess alcohol.

n-Propanol is the preferred alcohol for use herein. Other water miscible alcohols, such as methanol, ethanol, 2-propanol, and t-butanol, are considered to be useful as well. Where methanol or ethanol are used care must be taken to avoid evaporation which would alter the predetermined cholesterol concentration of the standard.

Betaine, an inner salt, has the following generally recognized structure:

$$(CH_3)_3N^+ - CH_2 - COO^-$$

Those long chain alkyl substituted betaines useful herein have at least one of the indicated methyl or the methylene groups replaced by a longer carbon chain group, e.g., about 8 to about 18 carbon atoms, inclusive. Betaines of the structure:

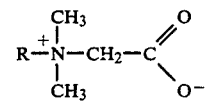

wherein R is an alkyl group containing 8 to 18 carbon atoms, are considered to be most useful. Preferably, in order to obtain ready solubility in both alcohol and water R is $C_{12}$ to $C_{16}$, inclusive.

Standards of the present invention are conveniently prepared by dissolving a predetermined amount of cholesterol in alcohol and then adding the betaine. To then achieve the desired cholesterol concentration addition of more alcohol followed, optionally, by water can be accomplished.

Standards containing up to about 800 mg of cholesterol per 100 ml of solution can be prepared in accordance with this invention, though ordinarily the maximum concentration will be 500 mg/100 ml solution. Per 500 ml of standard solution, there will in general be about 10 to 100 grams, preferably less than 50 grams, of betaine with at least about 250 ml of alcohol. Where alcohol consitutes less than 50%, by volume, of the solution, mechanical stability is sacrificed, particularly where the solution experiences alternating freeze/thaw cycles such as during shipping.

The following examples illustrate the preparation of standard solutions in accordance with the present invention.

EXAMPLE I

Place 1.2500 gm pure cholesterol in a 250 ml volumetric flask. Add 100 ml J. T. Baker Reagent Grade n-propanol. Add 50 ml Du Pont Product DDN (25% active n-laurylbetaine) and 50 ml more n-propanol. Dilute to a total volume of 250 ml solution with deionized water. Filter through Whatman #54 filter paper. Store in one polyethylene bottle and in one amber glass bottle.

EXAMPLE II

Place 2.5000 gm pure cholesterol in a 500 ml volumetric flask. Add 200 ml J. T. Baker Reagent Grade n-propanol and heat with swirling until all of the cholesterol dissolves. Then add 95.0 gm Ashland Varion CDG Coco betaine (32% active, pH 6.5 in water) with good mixing. Add 100 ml more n-propanol with good mixing and dilute to a total volume of 500 ml solution with deionized water. Filter through Whatman #54 filter paper and store in amber glass bottle.

EXAMPLE III

Example I is repeated except that the betaine used is Lonzaine 14, a betaine from Lonza Inc., wherein the long chain alkyl group distribution is about 40% $C_{12}$, 50% $C_{14}$, and 10% $C_{16}$.

All of the exemplified solutions have excellent long term mechanical stability and can be used in preparing aqueous calibrator solutions without precipitation of cholesterol. Example III is currently the preferred standard solution.

As illustrated, the standards contain 500 mg cholesterol per 100 ml solution. To form less concentrated solutions the standards can be diluted with water to a new volume. Preferably this should be done just prior to use.

While the present invention has been described in connection with certain preferred embodiments, it is to be understood that it is not to be limited to only those embodiments. On the contrary, it is intended to cover all modifications and alternatives falling within the spirit and scope of the invention as expressed in the appended claims.

We claim:

1. A standard solution useful in the quantitative determination of cholesterol consisting essentially of a predetermined amount of cholesterol, a water miscible alcohol present in an amount sufficient to dissolve said cholesterol to thereby form a solution, and a long chain alkyl substituted betaine solution in both water and alcohol and present in an amount such that said solution, as prepared, has extended mechanical stability and can be fashioned into an aqueous calibrator solution without precipitation of cholesterol.

2. The standard solution of claim 1 containing water in addition to the identified ingredients.

3. The standard solution of claim 1 wherein the alcohol is n-propanol.

4. The standard solution of claim 2 wherein the alcohol is n-propanol.

5. The standard solution of claim 1, 2, 3 or 4 wherein the betaine has the structure.

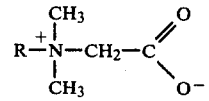

wherein R is an alkyl group containing 8 to 18 carbon atoms.

6. The standard solution of claim 5 wherein R contains 12 to 16 carbon atoms.

7. The standard solution of claim 1 wherein the respective concentrations of said cholesterol, said alcohol and said betaine in said solution is as follows:
Cholesterol: less than about 800 mg/dl
Alcohol: at least about 50% (V/V)
Betaine: between about 2–20 g/dl 8. The solution of claim 7 wherein said betaine concentration is less than about 10 g/dl.

9. A standard solution useful in the quantitative determination of cholesterol consisting essentially of water, a predetermined amount of cholesterol, at least about 50% by volume of said solution of n-propanol, and between about 2 and 20 g/dl of a betaine having the structure

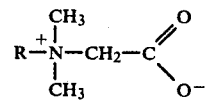

wherein R is an alkyl group containing 8 to 18 carbon atoms.

* * * * *

UNITED STATES PATENT AND TRADEMARK OFFICE
CERTIFICATE OF CORRECTION

PATENT NO. : 4,239,649
DATED : December 16, 1980
INVENTOR(S) : E. Melvin Gindler; Louis M. Mezei It is certified that error appears in the above-identified patent and that said Letters Patent are hereby corrected as shown below:

Col. 3, claim 1, line 6, "solution" should be --soluble--.

Signed and Sealed this

Tenth Day of March 1981

[SEAL]

Attest:

RENE D. TEGTMEYER

*Attesting Officer*   *Acting Commissioner of Patents and Trademarks*